(12) United States Patent
Roser et al.

US006964771B1

(10) Patent No.: US 6,964,771 B1
(45) Date of Patent: Nov. 15, 2005

(54) METHOD FOR STABLY INCORPORATING SUBSTANCES WITHIN DRY, FOAMED GLASS MATRICES

(75) Inventors: Bruce Roser, Cambridge (GB); Enda Martin Gribbon, Cambridge (GB)

(73) Assignee: Elan Drug Delivery Limited, Nottingham (GB)

( * ) Notice: Subject to any disclaimer, the term of this patent is extended or adjusted under 35 U.S.C. 154(b) by 587 days.

(21) Appl. No.: 08/923,783

(22) Filed: Sep. 4, 1997

Related U.S. Application Data

(63) Continuation of application No. 08/486,043, filed on Jun. 7, 1995.

(51) Int. Cl.⁷ .......................... A61K 9/00; A61K 47/00; A61K 9/20; A61K 9/14
(52) U.S. Cl. ...................... 424/400; 424/439; 424/464; 424/484; 435/2
(58) Field of Search ............................. 435/2; 424/464, 424/439, 400, 484

(56) References Cited

U.S. PATENT DOCUMENTS

| | | | |
|---|---|---|---|
| 3,362,830 A | | 1/1968 | Addesso |
| 3,557,717 A | * | 1/1971 | Chivers ........................ 107/54 |
| 3,619,294 A | * | 11/1971 | Black .......................... 127/30 |
| 3,632,357 A | * | 1/1972 | Childs ...................... 99/134 R |
| 3,655,442 A | * | 4/1972 | Schwer et al. ................ 127/58 |
| 3,667,962 A | | 6/1972 | Fritzberg et al. |
| 3,956,278 A | | 5/1976 | Prey |
| 4,127,502 A | * | 11/1978 | Li Mutti et al. ............. 252/408 |
| 4,158,544 A | * | 6/1979 | Louderback .................. 23/230 |
| 4,327,076 A | * | 4/1982 | Puglia et al. ................. 424/38 |
| 4,327,077 A | * | 4/1982 | Puglia et al. ................. 424/38 |
| 4,588,744 A | * | 5/1986 | McHugh ..................... 514/470 |
| 4,684,719 A | | 8/1987 | Nishikawa et al. |
| 4,701,417 A | * | 10/1987 | Portenhauser et al. ........ 436/13 |
| 4,762,857 A | * | 8/1988 | Bollin, Jr. et al. .......... 514/777 |
| 4,855,326 A | | 8/1989 | Fuisz |
| 4,865,871 A | * | 9/1989 | Livesey et al. ................ 427/4 |
| 4,883,762 A | * | 11/1989 | Hoskins ....................... 436/18 |
| 4,891,319 A | | 1/1990 | Roser |
| 5,026,566 A | | 6/1991 | Roser |
| 5,030,469 A | | 7/1991 | Mergelsberg |
| 5,149,653 A | | 9/1992 | Roser |
| 5,262,191 A | * | 11/1993 | Chakraborty et al. ....... 426/578 |
| 5,290,765 A | * | 3/1994 | Wettlaufer et al. ............ 514/23 |
| 5,306,506 A | | 4/1994 | Zema et al. |
| 5,348,852 A | * | 9/1994 | Bonderman .................... 435/4 |
| 5,364,756 A | * | 11/1994 | Livesey et al. ................ 435/2 |
| 5,380,473 A | | 1/1995 | Bogue et al. |
| 5,387,431 A | | 2/1995 | Fuisz |
| 5,422,384 A | * | 6/1995 | Samuels et al. ............. 523/170 |
| 5,425,951 A | | 6/1995 | Goodrich, Jr. et al. |
| 5,512,547 A | | 4/1996 | Johnson et al. |
| 5,516,763 A | * | 5/1996 | Heikkila et al. .............. 514/53 |
| 5,567,439 A | | 10/1996 | Myers et al. |
| 5,589,167 A | | 12/1996 | Cleland et al. |
| 5,766,520 A | | 6/1998 | Bronshtein |
| 5,955,448 A | * | 9/1999 | Colaco et al. ................ 514/53 |

FOREIGN PATENT DOCUMENTS

| | | |
|---|---|---|
| EP | 0 166 440 | 1/1986 |
| EP | 0166440 | 1/1986 |
| EP | 0 356 154 | 2/1990 |
| EP | 0 383 569 | 8/1990 |
| EP | 0415567 | * 3/1991 |
| EP | 0357665 | 3/1994 |
| EP | 0601965 | 6/1994 |
| EP | 0 714 905 | 6/1996 |
| EP | 0714905 | 6/1996 |
| GB | 1381588 | 1/1975 |
| GB | 1462168 | 1/1977 |
| GB | 2206273 | * 1/1989 |
| JP | 58-216695 | 12/1983 |
| WO | 8700196 | * 1/1987 |
| WO | WO 88/08298 | 11/1988 |
| WO | WO 89/06542 | 7/1989 |
| WO | WO 90/11756 | 10/1990 |
| WO | WO 91/18091 | 11/1991 |
| WO | 9202133 | * 2/1992 |
| WO | WO 93/02834 | 2/1993 |
| WO | WO 93/10758 | 6/1993 |
| WO | WO 93/11220 | 6/1993 |
| WO | 93/11220 | 6/1993 |
| WO | WO 94/22423 | 10/1994 |
| WO | WO 95/06126 | 3/1995 |
| WO | 9533488 | * 12/1995 |
| WO | 96/22107 | 7/1996 |
| WO | 96/40077 | 12/1996 |

OTHER PUBLICATIONS

Postavaru, "Foaming agents in the manufacture of some sugar confectionery products", Industria Alimentara 23 (11) : 631 (1972).*

Annear, D.I., "Recoveries of Bacteria After Drying and Hearing in Glutamate Foams" *Journal of Hygiene* (Mar. 24,, 1970) pp. 457–459.

Annear, D.I., "The Preservation of Bacteria By Drying In Peptone Plugs" *Journal of Hygiene*, vol. 54, No. 4, pp. 487–508 (1956).

Dialog® English Abstract of JP 58–216695 (Dec. 16, 1983).

Dialog® WPI File 351 Abstract of PCT WO 87/05300 (Sep. 11, 1987).

Sakurai, Y (ed.), "Food General Dictionary" Sixth Edition, 10 pages total.

Kanna et al., "Denaturation of Fish Muscle Protein by Dehydration –V." *Bull. Tokai Reg. Fish. Res. Lab.* (1974) 77:1–17.

(Continued)

*Primary Examiner*—Sandra E. Saucier
(74) *Attorney, Agent, or Firm*—Morrison & Foerster LLP (57) ABSTRACT

The invention provides methods for producing foamed glass and the compositions obtained thereby. The compositions are suitable for stable storage of a wide variety of substances, particularly biological and pharmaceutical.

13 Claims, 6 Drawing Sheets

OTHER PUBLICATIONS

Handbook of Natural Materials for Food Processing, Ninth Edition, pp. 384 and 495 with English translation.

Chemical Dictionary, 7, pp. 310–311 with English translation.

*Stability and characterization of protein and peptide drugs*, Wang et al., eds. 1993. Table of contents enclosed, pp. xv–xxi.

Goren et al., (α–D–Glucopyranosyluronic acid) (α–D–glucopyranosiduronic acid) and simple derivatives *Carbohydrate Res.* (1980) 79:225–234.

Schmidt, "New methods for the synthesis of glycosides and oligosaccharides—are there alternatives to the Koenigs–Knorr method?" *Angew. Chem. Int. Ed. Engl.* (1986)25:212–235.

Paulsen, "Advances in selective chemical syntheses of complex oligosaccharides" *Angew. Chemie* (1982) 21:155–173.

Streitwieser, Jr. et al., eds., "Carbohydrates" Introduction to Organic Chemistry (1976) Macmillan Publishing Co., New York, Chapter 25, pp. 693–732.

Pikal, "Freeze–drying of proteins. Process, formulation, and stability" *ACS Symposium Series, Formulation and Delivery of Proteins and Peptides* J.L. Cleland et al., eds., (1994) 567:120–133.

Carpenter et al., "Interactions of stabilizers with proteins during freezing and drying" *ACS Symposium Series, Formulation and Delivery of Proteins and Peptides* J.L. Cleland et al., eds.,(1994) 567:134–147.

Crowe et al., "Are freezing and dehydration similar stress vectors? A comparison of modes of interaction of stabilizing solutes with biomolecules" *Cryobiol.* (1990) 27:219–231.

Blakeley et al., "Dry instant blood typing plate for bedside use" *Lancet* (1990) 336:854–855.

Roser, "Trehalose, a new approach to premium dried foods" *Trends in Food Sci. and Tech.* (Jul. 1991) pp. 166–169.

Colaco et al., "Trehalose stabilisation of biological molecules" *Biotechnol. Internat.* (1992) pp. 345–350.

Roser, "Trehalose drying: A novel replacement for freeze–drying" *BioPharm.* (1991) 4:47–53.

Colaco et al., "Extraordinary stability of enzymes dried in trehalose: Simplified molecular biology" *Bio/Tech.* (1992) 10:1007–1011.

Roser et al., "A sweeter way to fresher food" *New Scientist* (1993) 138:25–28.

Crowe, et al., "Stabilization of biological membranes at low water activities" (1983) *Crybiol.* 20:346–356.

Argall et al., "The use of trehalose–stabilized lyophilized methanol dehydrogenase from Hyphomicrobium X for the detection of methanol" *Biochem. Mol. Biol. Int.* (1993) 30:491–497.

Hottiger et al., "The role of trehalose synthesis for the acquisition of thermotolerance in yeast. II. Physiological concentrations of trehalose increase the thermal stability of proteins in vitro" *Eur. J. Biochem.* (1994) 219:187–193.

Loomis et al., "Anhydrobiosis in nematodes: Inhibition of the Browning reaction of reducing sugars with dry proteins" *J. Exp. Zool.* (1979) 208:355–360.

Sanchez et al., Recombinant system for overexpression of cholera toxin B subunit in *Vibrio cholerae* as a basis for vaccine development *Proc. Natl. Acad. Sci. USA* (1989) 86:481–485.

Takahashi et al., "Induction of $CD8^+$cytotoxic T cells by immunization with purified HIV–1 envelope protein in ISCOMs" *Nature* (1990) 344:873–875.

Green, J.L. et al. (1989). "Phase Relations and Vitrification in Saccharide–Water Solutions and the Trehalose Anomaly," *J. Phys. Chem.* 93:2880–2882.

* cited by examiner

METHOD FOR STABLY INCORPORATING SUBSTANCES WITHIN DRY, FOAMED GLASS MATRICES

This application is a continuation of application Ser. No. 08/486,043, filed Jun. 7, 1995.

TECHNICAL FIELD

This invention relates to methods of making foamed glasses and compositions obtained thereby. More specifically, it relates to methods of stably incorporating substances, particularly biological substances, into dried foamed glass matrices (FGMs) and the compositions obtained thereby.

BACKGROUND OF THE INVENTION

Traditionally, the most common method of preserving biological substances which are unstable in solution at ambient temperatures, such as proteins and DNA, has been freeze-drying. This process involves placing the substance in solution, freezing the solution, and exposing the frozen solid to a vacuum under conditions where it remains solid and the water and any other volatile components are removed by sublimation. The resulting dried formulation contains the biological substance and any salts or other non-volatile materials added to the solution before drying. This drying method, conventionally used in the absence of effective alternatives, often results in significant losses. Pikal (1994) *ACS Symposium* 567:120–133. Furthermore, many of the various parameters within the freeze-drying process remain poorly characterized, sometimes resulting in the loss of whole batches at the production level.

In spite of the apparent ubiquity of freeze-drying, many freeze-dried substances are still unstable at ambient temperatures. Pikal (1994); Carpenter et al. (1994) *ACS Symposium* 567:134–147. Damage caused by this process may be circumvented, to a certain degree, by the use of cryoprotectants. Carpenter et al. (1994). However, cryoprotectants may subsequently react with the dried substance. This imposes inherent instability upon storage of the freeze-dried substances.

Other methods used to prepare dry, stable preparations of labile biological and chemical substances such as ambient temperature drying, crystallisation or co-precipitation also have drawbacks. Ambient temperature drying techniques eliminate the freezing step and associated freeze-damage to the substance. These techniques are more rapid and energy-efficient in the removal of water. Crowe et al. (1990) *Cryobiol.* 27:219–231. However, ambient temperature drying often yields denatured or even inactive substances unless an appropriate stabilizer is used. Crystallisation or co-precipitation can only be applied to a few substances, and the products of these methods have poor solubility. Additionally, there are problems in removing residual moisture.

Trehalose, α-D-glucopyranosyl- α-D-glucopyranoside, is a naturally occurring, inert, non-reducing and non-toxic disaccharide which was initially found to be associated with the prevention of desiccation damage in certain plants and animals which can dry out without damage and revive when rehydrated. Trehalose has been shown to be useful in preventing denaturation of a wide variety of substances such as proteins, viruses and foodstuffs during desiccation and subsequent storage. Formulations of products air dried in trehalose have been found to have a remarkably increased storage life. See U.S. Pat. Nos. 4,891,319; 5,149,653; 5,026, 566; Blakely et al. (1990) *Lancet* 336:854; Roser (July 1991) *Trends in Food Sci. and Tech.*, pp. 166–169; Colaco et al. (1992) *Biotechnol. Internat.*, pp. 345–350; Roser (1991) *BioPharm.* 4:47; Colaco et al. (1992) *Bio/Tech.* 10:1007; Roser and Colaco (1993) *New Scientist* 138:25–28; and Crowe (1983) *Cryobiol.* 20:346–356. Trehalose also stabilizes lyophilized proteins, such as methanol dehydrogenase (Argall and Smith (1993) *Biochem. Mol. Biol. Int.* 30:491), and to confer thermoprotection to enzymes from yeast. Hottiger et al. (1994) *Eur. J. Biochem.* 219:187. Trehalose also inhibits the Maillard reaction between carbonyl groups of reducing sugars and amino groups of proteins. Loomis et al. (1979) *J. Exp. Zool.* 208:355–360; and Roser and Colaco (1993) *New Scientist* 138:24–28. Trehalose and a wide variety of stabilizing polyols have also been found useful in formulation of solid dosages.

There is a serious need for a method to inexpensively and stably incorporate substances into glass matrices with a minimum of residual moisture remaining in the product. Such a process would provide products exhibiting increased stability, a longer shelf life, and facile rehydration. Facile rehydration would be a particular advantage for parenterally administered pharmaceutical substances.

All references cited herein are hereby incorporated by reference.

SUMMARY OF THE INVENTION

The present invention encompasses methods of producing dried foamed glass matrices (FGMs). The invention also includes methods of stably incorporating substances, including active substances, within FGMs. Also included in the present invention are compositions comprising FGMS, as well as compositions containing substances stably incorporated within FGMs.

Accordingly, one aspect of the invention is methods for producing FGMs, comprising preparing a mixture comprising at least one glass matrix-forming material in at least one solvent, evaporating bulk solvent from the mixture to obtain a syrup, exposing the syrup to a pressure and temperature sufficient to cause boiling of the syrup, and optionally removing residual moisture.

In another aspect of the invention, methods are provided for stably incorporating at least one substance within the FGMs. These methods include preparing a mixture comprising at least one solvent, at least one glass matrix-forming material and at least one substance to be incorporated, evaporating bulk solvent from the mixture to obtain a syrup, exposing the syrup to a pressure and temperature sufficient to cause boiling of the syrup, and optionally removing residual moisture. The substances that can be incorporated encompass active materials. The methods can be enhanced by the addition to the solution of various additives such as volatile salts, decomposing salts, organic solvents and viscosity modifiers.

Another aspect of the invention encompasses methods for producing stable, dried, readily soluble single dosages of a substance which is unstable in solution. These methods include preparing a mixture comprising at least one glass matrix-forming material and a substance in at least one solvent, evaporating bulk solvent from the mixture to obtain a syrup, exposing the syrup to a pressure and temperature sufficient to cause boiling of the syrup, and optionally removing residual moisture.

The invention encompasses compositions obtained by the methods described herein. The invention further encompasses compositions comprising FGMs and compositions comprising FGMs and any substance(s) stably incorporated therein.

In another aspect, the invention includes methods for reconstituting substances that are incorporated into the FGMs. The methods include adding a suitable solvent to the FGMs in an amount sufficient to attain the desired concentration of the substances incorporated therein.

MODES FOR CARRYING OUT THE INVENTION

It has now been found that glass matrix-forming materials can be processed into foamed glass matrices (FGMs) that are particularly useful for stably incorporating substances, such as active substances, particularly including bioactive substances. As used herein, a "substance" is any substance having an intended use that can be stored in a dry, non-liquid state.

The methods of this invention result in products with markedly reduced residual moisture content compared to thick, unfoamed glasses, resulting in a drier product with increased stability and higher glass transition temperatures. Further, the high surface area afforded by FGMs results in significantly increased dissolution rates on reconstitution. This is especially useful for low solubility substances such as organic substances, including, but not limited to, Cyclosporin A, lipids, esterified sugars, beta blockers, H2 agonists and antagonists, steroids, sex hormones, phenobarbitals, analgesics, antimicrobials, antivirals, insecticides, pesticides and the like. These methods produce products which provide all of the benefits and none of the drawbacks of freeze-drying. These drawbacks include, but are not limited to, long and energy-intensive drying processes using extremely low temperatures and increased product dissolution times. The products encompassed by the present invention are rapidly dissolved, with complete solubilization of the product that can be easily determined visually. The methods are straightforward, standardized, and reproducible.

Any material that can be formed into a glass matrix is suitable in this invention. Suitable materials include, but are not limited to, all polyols, including carbohydrate and non-carbohydrate polyols. Particularly suitable materials include sugars, sugar alcohols and carbohydrate derivatives.

FGMs are useful for storing any substance. FGMs are particularly useful for poorly soluble substances such as organic substances. Additionally, FGMs are particularly suitable for dyes, flavorings, biomolecules, molecular assemblies, cells and other unstable substances. In accordance with this invention, it is now possible to produce single-dosage units of bioactive substances which are storage stable at ambient and even elevated temperatures. Upon reconstitution, a single dosage of the bioactive substance is obtained. Single dosages can be, for instance, a single therapeutic dosage of a biological substance such as epinephrin, erythropoietin, cytokines, growth factors and other biopharmaceuticals or a single reaction mix such as that required for ovulation and pregnancy tests and other diagnostic kits.

The present invention encompasses methods of producing FGMS. The methods comprise the steps of preparing a mixture of at least one glass matrix-forming material in a solvent therefor, evaporating bulk solvent from the mixture to obtain a syrup, exposing the syrup to a pressure and temperature sufficient to cause boiling of the syrup and optionally removing residual moisture.

As used herein, "foamed glass matrix" ("FGM") is a high surface area foamed glass matrix. FGMs can be of varying thickness, including thin or ultra-thin. Typically, the FGM is much less dense than the solid dosage amorphous glass, because of the increased surface area and the thinness of glass forming the bubble walls of the foamed glass matrix.

Preferably, the glass matrix-forming material is a stabilizing polyol and more preferably it is a carbohydrate and derivatives thereof, including trehalose, lactitol and palatinit. Most preferably, the stabilizing polyol is trehalose. Suitable stabilizing polyols are those in which a desired substance can be dried and stored without substantial losses in activity by denaturation, aggregation or other mechanisms.

As used herein, the term "carbohydrates" includes, but is not limited to, monosaccharides, disaccharides, trisaccharides, oligosaccharides and their corresponding sugar alcohols, polyhydroxy compounds such as carbohydrate derivatives and chemically modified carbohydrates, hydroxyethyl starch and sugar copolymers. Both natural and synthetic carbohydrates are suitable for use herein. Synthetic carbohydrates include, but are not limited to, those which have the glycosidic bond replaced by a thiol or carbon bond. Both D and L forms of the carbohydrates may be used. The carbohydrate may be non-reducing or reducing.

Prevention of losses of activity can be enhanced by the addition of various additives such as inhibitors of the Maillard reaction as described below. Addition of such inhibitors is particularly preferred in conjunction with reducing carbohydrates.

Reducing carbohydrates suitable for use in the present invention are those known in the art and include, but are not limited to, glucose, maltose, lactose, fructose, galactose, mannose, maltulose, and lactulose. Non-reducing carbohydrates include, but are not limited to, non-reducing glycosides of polyhydroxy compounds selected from sugar alcohols and other straight chain polyalcohols. Other useful carbohydrates include raffinose, stachyose, melezitose, dextran, sucrose, cellibiose, mannobiose and sugar alcohols. The sugar alcohol glycosides are preferably monoglycosides, in particular the compounds obtained by reduction of disaccharides such as lactose, maltose, lactulose and maltulose.

Particularly preferred carbohydrates are trehalose, maltitol (4-O-β-D-glucopyranosyl-D-glucitol), lactitol (4-O-β-D-galactopyranosyl-D-glucitol), palatinit (a mixture of GPS (α-D-glucopyranosyl-1→6-sorbitol) and GPM (α-D-glucopyranosyl-1→6-mannitol)], and its individual sugar alcohol components GPS and GPM.

Figure 1:
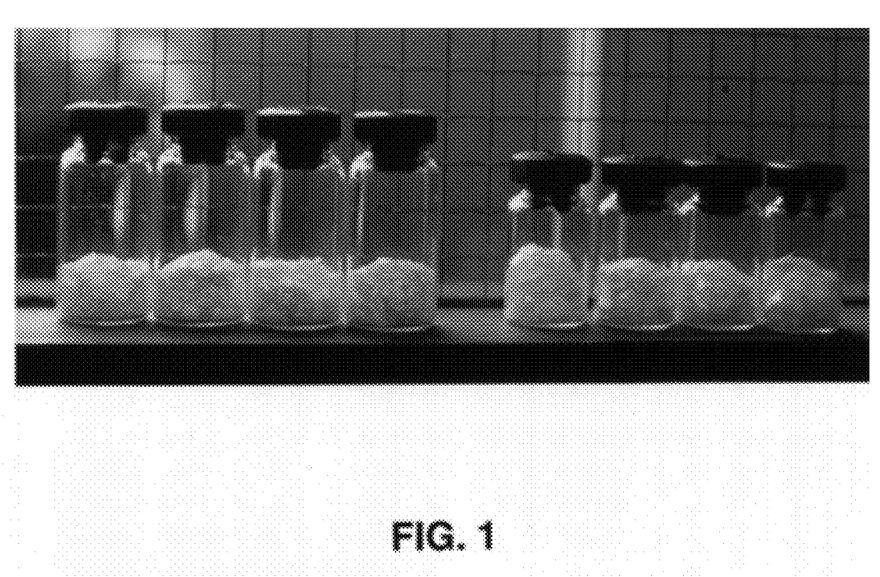
FIG. 1 is a photograph depicting FGMs formed in two differently sized pharmaceutical vials.

Different mixtures and various container shapes and sizes can be processed simultaneously. Ideally, the container size used is sufficient to contain the initial mixture and accommodate the volume of the FGM formed thereof. Typically, this is determined by the mass of the glass matrix-forming material, the surface area of the container and the conditions of FGM formation. The mass of glass matrix-forming material must be sufficient to give a viscous syrup to be foamed which translates practically as a minimal mass per unit area of container surface. This ratio varies from mixture to mixture and container used but is easily determined empirically by one skilled in the art by following the procedures set forth herein. Any such vials can be used, including Wheaton moulded and tube-cut vials. FIG. 1 is an illustration of FGMs formed in differently sized vials.

Although singular forms may be used herein, more than one glass matrix-forming material, more than one additive, and more than one substance may be present. Effective amounts of these components are easily determined by one of skill in the art.

The solvent into which the glass matrix-forming material is mixed can be aqueous, organic, or a mixture of both. The use of combinations of organic and aqueous solvents can provide an additional benefit, as the use of a volatile organic enhances the foamed glass formation. Enhanced foamed glass formation can also be achieved by using a volatile or decomposing salt as discussed below. Additionally, sufficient aqueous solvent to dissolve the glass matrix-forming material and sufficient organic to dissolve a hydrophobic substance may be used, allowing the formation of FGMs incorporating hydrophobic substance(s).

The choice of solvent will depend upon the nature of the material chosen for glass matrix formation, as well as the nature of any additive and/or substance to be incorporated. The solvent should be of a nature and of sufficient volume to effect adequate solubilization of the glass matrix-forming material as well as any additive and/or substance. If the substance is a hydrophilic material, the liquid will preferably be aqueous to avoid any potential loss of activity due to deleterious solvent interactions. Preferably, the aqueous solvent includes any suitable aqueous solvent known in the art, including, but not limited to, water and biological buffer solutions. Preferably, the aqueous solvent is present in an amount of 5 to 95% by volume.

The volume of the solvent can vary and will depend upon the glass matrix-forming material and the substance to be incorporated as well as any additives.

The minimum volume required is an amount necessary to solubilize the various components. However, homogeneously dispersed suspensions of the substance(s) can also be used. Suitable amounts of the components in specific embodiments are easily determinable by those skilled in the art in light of the examples provided herein.

Various additives can be put into the glass matrix-forming material. Typically, the additives enhance foam formation and/or the drying process or contribute to the solubilization of the substance. Alternatively, the additive contributes to the stability of the substance incorporated within the FGM. One or more additives may be present.

Figure 3:
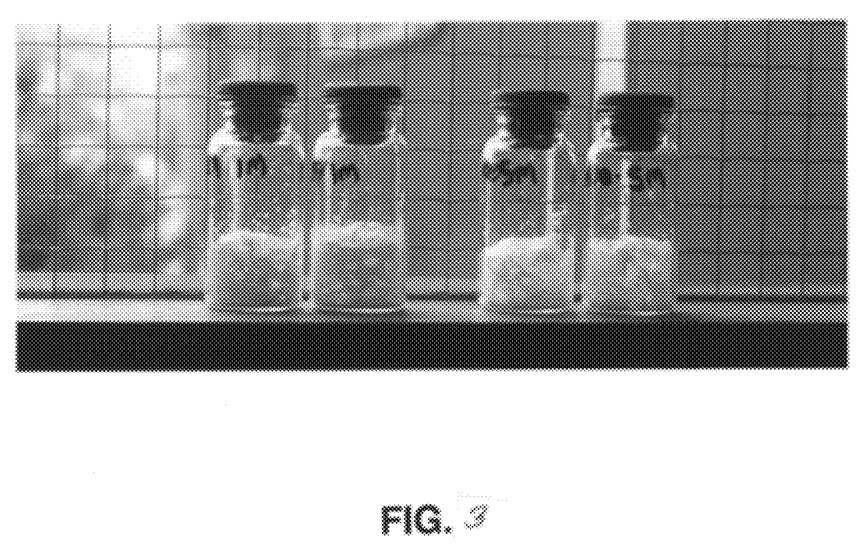
FIG. 3 is a photograph depicting the effect of volatile salts on FGM formation.

As an example, addition of volatile salts allows larger initial volumes and results in a higher surface area within the FGMs, thus effecting superior foam formation and more rapid drying. As used herein, volatile salts are salts which volatilize under the conditions used to produce FGMs. Examples of suitable volatile salts include, but are not limited to, ammonium acetate, ammonium bicarbonate and ammonium carbonate. Salts that decompose to give gaseous products also effect enhanced foam formation and more rapid drying. Examples of such salts are sodium bicarbonate and sodium metabisulphite. Preferably, the volatile salts are present in an amount of from about 0.01 to 5 M. Concentrations of up to 5 M are suitable for use herein. The resultant FGMs have uniform foam conformation and are significantly drier compared to FGMs in which volatile salts are not used. The effect of volatile salts on FGM formation is shown in FIG. 3 (see Example 3).

Volatile organic solvents can also be used in the initial mixture in order to improve the formation of FGMs. Examples of suitable volatile organic solvents include, but are not limited to, alcohols, ethers, oils, liquid hydrocarbons and their derivatives. While the volatile organic solvent may be used as the sole solvent for the glass matrix-forming material and/or substance, they are more commonly used in aqueous/organic mixtures. Preferably, the aqueous component of the mixture comprises between 5–80% by weight of the mixture, and more preferably comprises 10–50% by weight.

Figure 4:
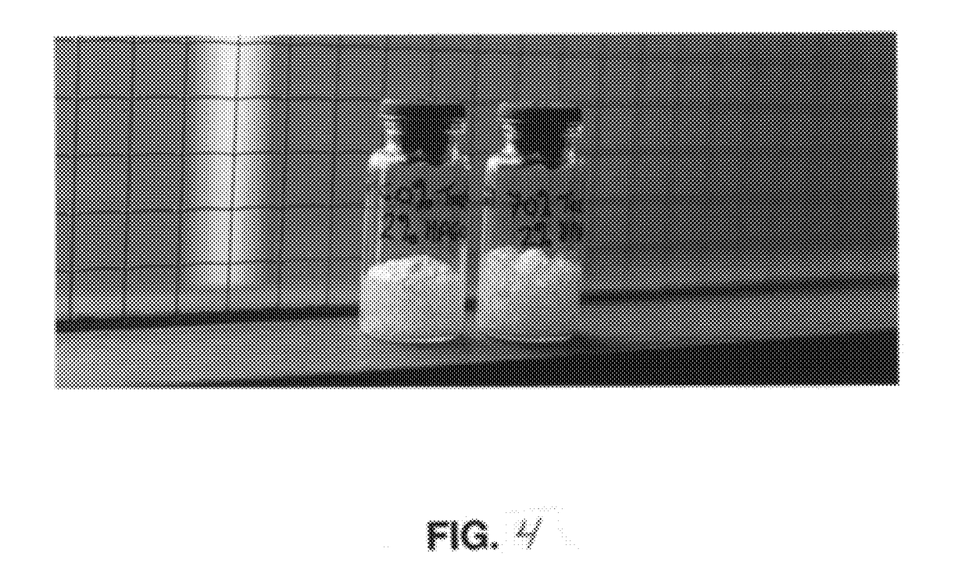
FIG. 4 is a photograph depicting the effect of varying viscosity on FGM formation.
Figure 5:
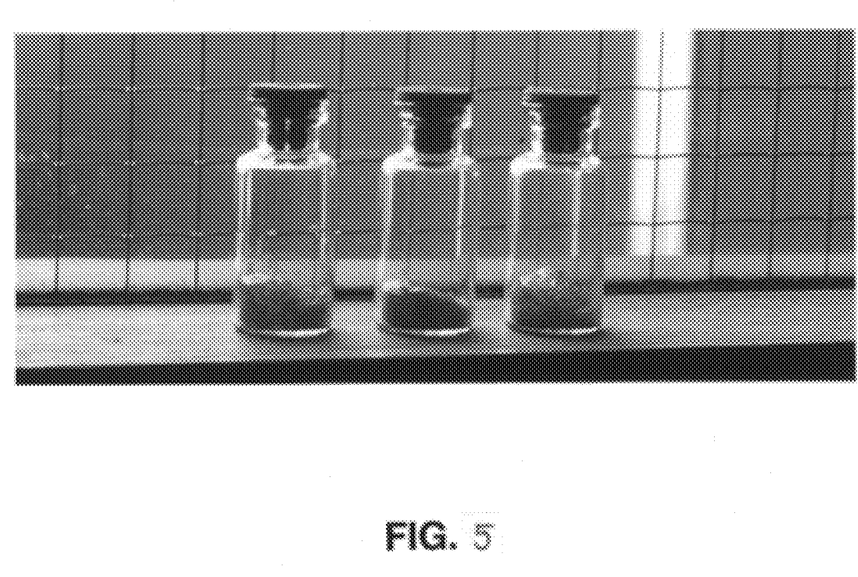
FIG. 5 is a photograph depicting FGMs containing human red blood cells.

Another suitable additive is a foam stabilizing agent, which can be used in combination with either the volatile or decomposing salt and/or organic solvent. This may either be a surface active component such as an amphipathic molecule (e.g., phospholipids) or an agent to increase the viscosity of the foaming syrup, such as a thickening agent such as guar gum and their derivatives. FIG. 4 illustrates the effect of varying viscosity on FGM formation (Example 3).

Another additive is an inhibitor of the Maillard reaction. Preferably, if the substance and/or glass matrix-forming material contains carbonyl and amino, imino or guanidino groups, the compositions further contain at least one physiologically acceptable inhibitor of the Maillard reaction in an amount effective to substantially prevent condensation of amino groups and reactive carbonyl groups in the composition. The inhibitor of the Maillard reaction can be any known in the art. The inhibitor is present in an amount sufficient to prevent, or substantially prevent, condensation of amino groups and reactive carbonyl groups. Typically, the amino groups are present on the substance and the carbonyl groups are present on the glass matrix forming material, or the converse. However, the amino and carbonyl groups may be intramolecular within either the substance or the carbohydrate. Various classes of compounds are known to exhibit an inhibiting effect on the Maillard reaction and hence to be of use in the compositions described herein. These compounds are generally either competitive or noncompetitive inhibitors of the Maillard reaction. Competitive inhibitors include, but are not limited to, amino acid residues (both D and L), combinations of amino acid residues and peptides. Particularly preferred are lysine, arginine, histidine and tryptophan. Lysine and arginine are the most effective. There are many known noncompetitive inhibitors. These include, but are not limited to, aminoguanidine and derivatives and amphotericin B. EP-A-O 433 679 also describes suitable Maillard inhibitors which include 4-hydroxy-5,8-dioxoquinoline derivatives.

Substances to be incorporated into the FGMs are added to the mixture before the foaming step. A wide variety of substances can be incorporated. For example, bioactive substances such as pharmaceutical agents and biological modifiers, as well as whole cells such as red blood cells and platelets, can be processed according to the methods described herein.

Any substance that can be homogeneously suspended in a solution of a solvent and glass matrix-forming material can be processed using these methods. FGMs have a greatly increased surface area compared to the mixture, a solid dosage form or any previously described composition. The increased surface area allows facile dissolution and therefore this invention is applicable to a large number of substances. Determining whether a substance is suitable for use herein is within the skill of one in the art, and the examples provided here are illustrative and non-limiting. By foaming a homogeneous suspension, areas of unevenly distributed substance, which could be deleterious for dissolution, are avoided in FGMs. More preferably, the substance will be solubilized in the solvent used in the initial mixture.

Examples of substances that can be incorporated within the FGMs include any bioactive substances such as pharmaceutically effective substances, including, but not limited to, antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antimicrobial agents, appetite suppressants, anticholinergics, antiemetics, antihistaminics, antimigraine agents, coronary, cerebral or peripheral vasodilators, hormonal agents, contraceptives, antithrombotic agents, diuretics, antihypertensive agents, cardiovascular drugs, opioids, and the like.

Suitable substances also include therapeutic and prophylactic agents. These include, but are not limited to, any therapeutically effective biological modifier. Such substances include, but are not limited to, subcellular compositions, cells, bacteria, viruses and molecules including, but not limited to, lipids, organics, proteins and peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein nucleic acid hybrids, small molecules and physiologically active analogs thereof. Further, the modifiers may be derived from natural sources or made by recombinant or synthetic means and include analogs, agonists and homologs. As used herein "protein" refers also to peptides and polypeptides. Such proteins include, but are not limited to, enzymes, biopharmaceuticals, growth hormones, growth factors, insulin, antibodies, both monoclonal and polygonal and fragments thereof, interferons, interleukins and cytokines. Organics include, but are not limited to, pharmaceutically active moieties with aromatic, carbonyl, amino, imino and guanidino groups. Suitable steroid hormones include, but are not limited to, estrogen, progesterone, testosterone and physiologically active analogs thereof. Numerous steroid hormone analogs are known in the art and include, but are not limited to, estradiol, SH-135 and tamoxifen. Many steroid hormones such as progesterone, testosterone and analogs thereof are particularly suitable for use in the present invention. Therapeutic agents prepared by the methods described herein are also encompassed by the invention. As used herein, "nucleic acids" includes any therapeutically effective nucleic acids known in the art including, but not limited to DNA, RNA and physiologically active analogs thereof. The nucleotides may encode genes or may be any vector known in the art of recombinant DNA including, but not limited to, plasmids, retroviruses and adeno-associated viruses.

Substances which are prophylactically active and carriers therefor are further encompassed by the invention. Preferable compositions include immunogens such as vaccines. Suitable vaccines include, but are not limited to, live and attenuated viruses, nucleotide vectors encoding antigens, live and attenuated bacteria, antigens, antigens plus adjuvants and haptens coupled to carriers. Particularly preferred are vaccines effective against diphtheria, tetanus, pertussis, botulinum, cholera, Dengue, Hepatitis A, B, C and E, hemophilus influenza b, herpes virus, *Helicobacterium pylori*, influenza, Japanese encephalitis, meningococci A, B and C, measles, mumps, papilloma virus, pneumococci, polio, rubella, rotavirus, respiratory syncytial virus, Shigella, tuberculosis, yellow fever and combinations thereof. The antigenic component of vaccines may also be produced by molecular biology techniques to produce recombinant peptides or fusion proteins containing one or more portions of a protein derived from a pathogen. For instance, fusion proteins containing an antigen and the B subunit of cholera-toxin have been shown to induce an immune response to the antigen. Sanchez et al. (1989) *Proc. Natl. Acad. Sci. USA* 86:481–485. Vaccines are particularly suitable for incorporation into the single-dosage composition. They are stable indefinitely under ambient conditions and can be redissolved in sterile diluent immediately before inoculation.

Preferably, the immunogenic composition contains an amount of an adjuvant sufficient to enhance the immune response to the immunogen. Suitable adjuvants include, but are not limited to, aluminum salts, squalene mixtures (SAF-1), muramyl peptide, saponin derivatives, mycobacterium cell wall preparations, monophosphoryl lipid A, mycolic acid derivatives, nonionic block copolymer surfactantsi Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant can be used.

As with all immunogenic compositions, the immunologically effective amounts of the immunogens must be determined empirically. Factors to be considered include the immunogenicity, whether or not the immunogen will be complexed with or covalently attached to an adjuvant or carrier protein or other carrier, route of administration and the number of immunizing dosages to be administered. Such factors are known in the vaccine art and it is well within the skill of immunologists to make such determinations without undue experimentation.

The substance can be present in varying concentrations in the FGMs. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is preferably one which will provide a single therapeutically effective dosage. Supersaturated solutions can also be used if the FGM is formed prior to crystallization. For bioactive substances, the minimum concentration is an amount necessary for bioactivity upon reconstitution and the maximum concentration is the point at which a homogeneous suspension cannot be maintained. In the case of single-dosage units, the amount is that of a single therapeutic application. For instance, Neupogen® is delivered at a dosage of 300 $\mu$g ($1\pm0.6\times10^8$ U/mg; 5 $\mu$g/kg/day). Thus, 300 $\mu$g would be processed per vial to provide a single dosage format. The preferred amount of the substance varies from substance to substance but is easily determinable by one of skill in the art.

In the primary drying step, the solvent is evaporated to obtain a syrup. Typically, a "syrup" is defined as a solution with a viscosity in the region of $10^6$–$10^7$ Pascal seconds. The syrup is not defined as a fixed concentration, but is a result of the bulk of the solvent evaporating from the mixture. Typically, a syrup is a viscous mixture containing the glass matrix-forming material and/or additives and/or substances, in a significantly higher concentration than that of the initial mixture. The evaporation step may remove 5–95% of the solvent. Typically, the evaporation step is conducted under conditions sufficient to remove about 20% to 90% of the solvent to obtain a syrup. The temperature can be about 0° C. to 80° C., or about 15° C. to 60° C., or about 25° C. to 45° C. The viscosity of the syrup is preferably such that when the syrup boils, evaporation from the increased surface area, provided by extensive bubble formation, results in its vitrification.

The preferred consistency of the syrup is dependent on the FGM desired for a particular application. The bubble size is controlled by the viscosity, rate of boiling and volatile component(s) or foam stabilizer if used.

The length of the initial drying step depends on the volume of solvent and the concentrations of the glass matrix-forming material(s) and any additives and/or substance(s) in the initial mixture, as well as the external temperature and pressure. For a given pressure, the rate of solvent evaporation increases with external temperature. Because the evaporative process has a cooling effect on the sample itself, the external temperature can be raised to increase the evaporation rate without affecting sample temperature. However, the rate of evaporation within the sample is inversely proportional to viscosity. As solvent is removed from the sample, the rate of evaporation thus decreases. This in turn allows an increase in sample temperature to the boiling point at reduced pressure.

The initial drying step can be performed under pressure less than ambient. Preferably, the pressure is 0.1 to 30 Torr/mm Hg. Even more preferably, the pressure is 5 to 20 Torr/mm Hg. Most preferably, the pressure is 7.5 to 12.5 Torr/mm Hg and the external temperature is 40° C. Aqueous or organic solutions, or mixtures thereof can be processed under these conditions. Dilute solutions with concentrations of 10–50% (w/v) are also suitable for processing under these conditions.

Reduction of the external pressure has at least two desirable effects. Firstly, it reduces the vapor pressure of the solvent in the gas phase, thus accelerating evaporation and drying. The increased rate of evaporation causes evaporative cooling of the samples unless external heat is applied to replace the latent heat of evaporation. Under vacuum, the rate of drying is limited by this energy input. Thus, the effect of increasing the external temperature is, surprisingly, to accelerate the rate of drying and not to increase the sample temperature. The second effect of reduced external pressure is to drastically lower the boiling point of the sample. Boiling can therefore be conducted by a very modest rise in sample temperature which does not have a deleterious effect on the product.

The syrup obtained from the primary drying step is exposed to a reduced pressure to effect boiling of the syrup. As used herein, "boiling" is defined as the point at which the vapor pressure of the mixture is equal to or exceeds the external pressure to which the sample is exposed. Boiling is evidenced visually by bubbling as the solvent and/or other volatile components rapidly vaporize. Typically, the most important factor determining sample boiling temperature is the external pressure. If a lower boiling point is desired to preserve the integrity of the substance, the external pressure is chosen is less than atmospheric (i.e., a vacuum), thus lowering the temperature required for boiling. Because the boiling step is thus achieved at lower temperatures, the integrity of the substance is not jeopardized.

If reduced pressure is used, rapid drying continues until the viscosity of the sample begins to increase. At this point, the reduced mobility of water molecules through the viscous syrup reduces the rate of evaporative cooling and the sample temperature rises until it reaches the boiling point at the reduced pressure. On boiling, a large increase in the area of the liquid/gas interface occurs due to the bubbling of the syrup. This increased evaporative surface causes a sharp increase in the drying rate and the liquid foam dries into solid glass foam. Typically, this occurs soon after boiling.

Temperatures for the boiling step can be above or below ambient temperature. A temperature of 0° C. to 80° C. can be used. Preferably, the external temperature for the boiling step is 5 to 80° C. Most preferably, the external temperature is 15 to 60° C.

Figure 2:
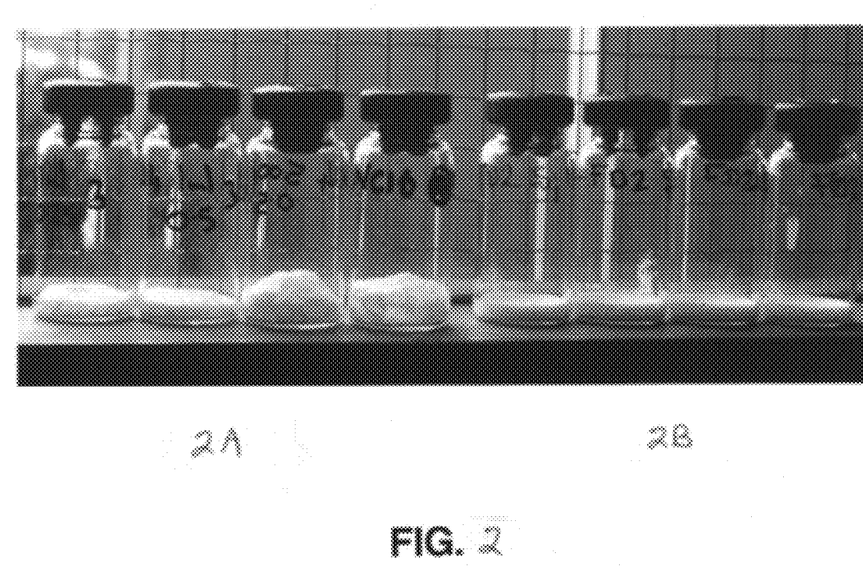
FIG. 2 is a photograph depicting the effect of varying pressures on FGM formation (FIG. 2A) and comparison to freeze-drying (FIG. 2B). The samples in FIG. 2B were of identical composition to those of FIG. 2A, except that the samples in FIG. 2A were formed into FGMs by the methods described herein, while the samples in FIG. 2B were freeze-dried.

Preferably, the external pressure during the boiling step is 20 to 0.01 Torr/mm Hg. More preferably, the external pressure is 0.1 to 0.05 Torr/mm Hg. FIG. 2 shows the effect of varying vacuum pressure on FGM formation. For creation of a vacuum, any vacuum drier with control, preferably programmable control, of the vacuum pressure and external temperature can be used. The pump must be capable of providing a vacuum of 0.01 Torr/mm Hg and evacuating the product chamber down to 0.2–0.01 Torr/mm Hg in 15–20 mins. The machines used in the present work were the FTS Systems Inc. (Stone Ridge, N.Y.) Model TDS 00078-A with a VP-62P vacuum pump and a FD-00057-A condenser module or the Labconco, Inc. (Kansas City) Model No 77560 with a Lyph-Lock 12 condenser unit and an Edwards E2M8 two-stage vacuum pump.

The boiling step results in formation of bubbles which greatly increases the evaporative surface area of the syrup. This allows increased evaporation of residual solvent and the FGM vitrifies as a solid foam of the bubbles which result from the boiling step. The endpoint of the boiling step can be determined by an increase in sample temperature, which is preferably maintained for a period to ensure complete drying. This varies from sample to sample but is easily determinable by one of skill in the art.

Residual moisture may be optionally removed to assure complete drying. This step typically occurs at elevated temperature and/or reduced pressure. FGM with residual moisture content of 0.1 to 12% (w/w) can be achieved. Preferably, the final product should have a residual moisture content of approximately 0.1–5% (w/w). Preferably, the residual moisture is removed within 1–15 hours. The residual moisture is removed in shorter times at elevated temperatures.

Because the formation of the FGMs occurs via bubble formation, the random bubble arrangement and size may give rise to regions of variable residual moisture content. Thus, during the secondary drying step, some regions will dry much more readily than others. As has been discussed above, the presence of a volatile or decomposing salt and/or volatile organic solvent results in an FGM with small, uniform bubble size, which leads to lower residual moisture content and a more homogeneous distribution thereof.

Materials incorporated in trehalose glasses can be stored at ambient temperatures for at least 3 years. Active substances incorporated in glasses formed from other polyols can also show extended storage stabilities.

The FGMs can be reconstituted immediately upon addition of suitable solvent. Thus, the invention includes methods of reconstituting substances that have been incorporated into the FGMs. The nature and amount of the solvent will depend upon the type and amount of substance to be reconstituted, as well as the intended use of the reconstituted substance. Typically, a minimum amount of solvent, in an amount necessary to effect solubilization of the glass matrix and the substance will be added. If the substance is a pharmaceutical or bioactive, reconstitution is preferably with a biologically acceptable buffer. Reconstitution can be performed at any temperature, provided it does not substantially hare the activity of the substance. Preferably, reconstitution is at ambient temperatures.

The invention also encompasses single-dosage units of active substances which are storage stable at ambient and even elevated temperatures (in some instances up to 100° C.) and which upon reconstitution with a premeasured aliquot of a suitable, preferably sterile solvent, forms a therapeutically effective dosage of the substance. This is especially effective for use with therapeutics, including purified and recombinant proteins and active substances, such as bioactives, which are normally stable in solution only at or below 4–8° C. Compositions of single-dosage (or multiple dosage) formats for more stable products, units and kits containing one or more single-dosage units and aliquots (preferably premeasured) of suitable solvent are also encompassed by this invention. Active substances which would be particularly suitable for storage and reconstitution using the method of this invention include, but are not limited to, Factor VIII, Neupogen®, Epogen®, TPA, cytokines, growth hormones, growth factors, vaccines, lipids, enzymes and other biopharmaceuticals, as well as other parenterally administered active substances.

The invention further encompasses compositions comprising the glass matrix obtained by the methods described herein. The compositions include, but are not limited to FGM(s); FGM(s) with various substances incorporated therein; and reconstituted substances obtained from FGM(s).

The following examples are provided to illustrate by not limit the present invention.

EXAMPLE 1

Effect of Vacuum Pressure and External Temperature on Primary Drying Times 2 ml aliquots of 10% (w/v) trehalose in deionized distilled water were placed in 10 ml Wheaton pharmaceutical vials and dried in an FTS drier at various vacuum pressures and shelf temperature settings. The sample temperatures and the time taken to remove approximately 90% of the water (i.e. primary drying to give a syrup) were determined.

EXAMPLE 2

Formation of FGMs

2a. Formation From an Aqueous Solution of Glass Matrix-forming Material

Aliquots of 250, 410 μl and 500 μl of a 50% (w/v) solution of trehalose in 3 ml, 5 ml and 10 ml pharmaceutical vials respectively, were dried in an FTS drier for 16 hrs. The shelf temperature was maintained at 25° C. throughout the run and the vacuum pressure dropped to 0.03 Torr/mm Hg within the first 15 mins of the run and maintained at 0.03 Torr/mm Hg throughout the run. The FGMs formed are shown in FIG. 1A. The foam-like appearance is due to the instantaneous drying of the bubbles that form during the boiling step.

2b. Formation From an Aqueous Solution of Glass Matrix-forming Materials Incorporating Active in Solution Recombinant Hepatitis B Surface Antigen in 20% (w/v) trehalose ±0.5% (w/v) Byco A in PBS was dried in 300 μl volumes in 3 ml pharmaceutical vials. The FTS drying protocol involved a pressure of 0.03 Torr/mm Hg with shelf temperature maintained at 40° C. throughout a drying cycle of 18 hours. The mean residual moisture contents of FGMs was in the region of 4% w/w.

2c. Formation From an Organic Solution of Glass Matrix-forming Material

Figure 6:
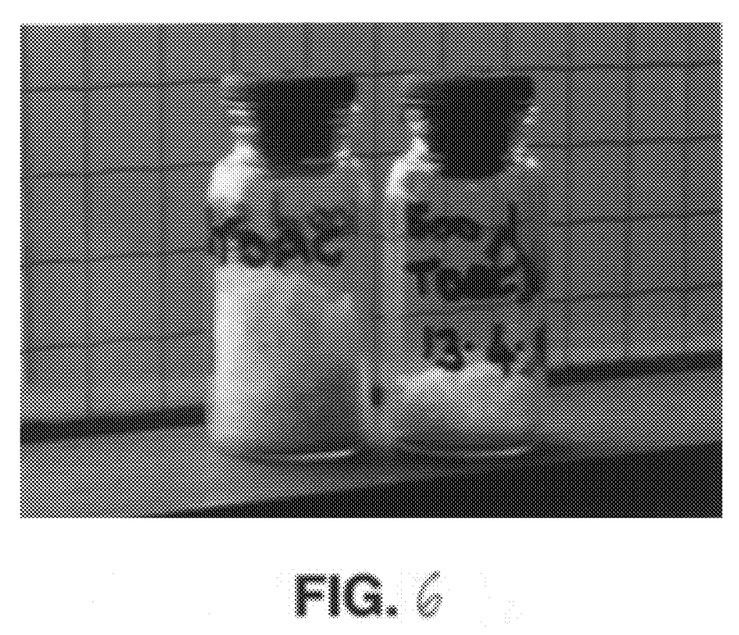
FIG. 6 is a photograph depicting FGMs of trehalose octaacetate made from organic solution.

500 μl aliquots of 50% (w/v) trehalose octaacetate in dichloromethane were dried in 10 ml pharmaceutical vials. Shelf temperature and pressure were maintained at 30° C. and 0.03 Torr/mm Hg respectively, throughout the 16 hour drying cycle. The FGMs formed are shown in FIG. 6. Rapid dissolution of the FGMs was observed on reconstitution.

2d. Formation From an Aqueous/organic Mixture Containing Glass Matrix-forming Material and Active Substance 750 μl aliquots of a 2:1 mixture of 50% (w/v) trehalose in deionized distilled water and 100 mg/ml of an organic active substance, the anaesthetic atracurium, in ethanol was dried in 10 ml pharmaceutical vials in the FTS drier. Shelf temperature and pressure were maintained at constant values of 40° C. and 0.03 Torr/mm Hg respectively, throughout the 18 hour drying cycle. Reconstitution of the FGMs in 20% v/v ethanol in deionized distilled water, resulted in rapid dissolution to give a homogeneous solution of the anaesthetic.

2e. Formation From an Aqueous Solution of Glass Matrix-forming Material, Plus Additive, Incorporating Active Substance in Homogeneous Suspension The inorganic active substance, the adjuvant aluminium hydroxide, was dried at suspension concentrations of either 2.5 or 6 mg/ml, in either PBS or 0.9% (w/v) saline as the solvent for the glass matrix-forming material, using the following formulations which contained a volatile salt additive to improve FGM formation (see Example 4);

i) 20% (w/v) trehalose±ammonium bicarbonate
ii) 50% (w/v) trehalose±ammonium bicarbonate
iii) 38.5% (w/v) maltose±ammonium bicarbonate
iv) 25% (w/v) trehalose±ammonium bicarbonate 250 and 300 μl samples, containing a range of ammonium bicarbonate concentrations from 0.05–0.75 M, were dried in 3 ml pharmaceutical vials using one of the two following FTS protocols:

1) pressure was reduced to 0.03 Torr/mm Hg and shelf temperature raised at 2 hour intervals from 35° C. to 50° C. and finally 60° C. Total cycle time was approximately 18 hours. Resultant FGMs had residual moisture contents in the range of 1.5–2.9% w/w. Reconstitution of the FGMs was instantaneous.

2) pressure was held at 15 Torr/mm Hg for 30 minutes prior to decreasing to 10 Torr/mm Hg for 30 minutes. Shelf temperature was raised from 10° C. to 25° C. Pressure was reduced to 0.03 Torr/mm Hg/mm Hg and held at this for approximately 18 hours. During this stage shelf temperature was raised from 25° C. to 45° C. and 2 hours later to 60° C. The resultant FGMs resembled freeze-dried plugs and rehydration was again instantaneous. These results also illustrate the effect of shelf temperature and vacuum pressure (see Example 3) and volatile salt additive (see Example 4) on FGM formation, appearance and residual moisture contents.

EXAMPLE 3

Effect of Vacuum Pressure/Shelf Temperature on FGM Formation

3a. Formation From Solution of Glass Matrix-forming Material Plus Additive

Aliquots of 1 ml or 500 μl of 25% (w/v) trehalose containing either 0.25 or 0.5 M ammonium bicarbonate, were dried in 10 ml pharmaceutical vials in the FTS drier. The 1 ml samples were dried at a constant vacuum pressure of 0.03 Torr/mm Hg for 14 hrs, with shelf temperature initially 25° C., raised to 45° C. after the first 2 hours (i.e., syrup formed). The 500 µl samples were dried at a constant shelf temperature of 25° C. and a constant vacuum pressure of 0.01 Torr/mm Hg for 14 hr. The FGMs formed (FIG. 2A) occupied larger volumes than identical samples processed by freeze-drying (FIG. 2B).

3b. Formation From Solution of Glass Matrix-forming Material Incorporating an Active 300 µl aliquots of a solution of 43.4 mg/ml trehalose containing 66 mg/ml of an antimicrobial peptide was dried in 10 ml polypropylene tubes (10 mm diameter) in the FTS drier. Samples, at 25° C., were loaded onto a shelf that had been preheated to 35° C. The vacuum pressure in the chamber was progressively reduced to 20 Torr/mm Hg over 10 minutes. This pressure was held for a further 30 minutes before the pressure was further reduced to 0.03 Torr/mm Hg. After 981 minutes the shelf temperature was increased to 50° C. This shelf temperature was maintained for 190 minutes after which the cycle was stopped. The FGMs produced have an open plug-like structure similar to freeze-dried materials. Moisture content was 1.1 to 1.3% (w/w). Dissolution was instantaneous on reconstitution. Similar FGMs were produced by the use of sucrose or GPS instead of trehalose. Elevated temperature storage of the FGMs containing trehalose as the glass matrix-forming material at 60° C. and at ambient humidity showed no shrinking over a period of more than 30 days and the FGM structure remained intact. Dissolution of samples remained instantaneous even after storage.

EXAMPLE 4

Effect of Additives on FGM Formation

4a. Effect of Volatile Salt Additive on FGM Formation

500 µl aliquots of 3–60% (w/v) trehalose in deionized distilled water containing a range of concentrations of 0–4 M Ammonium acetate or bicarbonate were dried in the. FTS drier. Shelf temperature was maintained constant at 20° C. and vacuum pressure at 0.03 Torr/mm Hg for the 18 hours drying cycle. Residual moisture contents of the FGMs formed were in the range of 2–5.5% (w/w) and rehydration was instantaneous on reconstitution. An example of the FGMs formed is shown in FIG. 3.

4b. Effect of Decomposing Salt Additive on FGM Formation

500 µl aliquots of 50% (w/v) trehalose±1M Sodium metabisulphite were dried in an FTS drier for either 12 or 18 hours. Shelf temperature and pressure were maintained at a constant 40° C. and 0.03 Torr/mm Hg respectively, throughout the drying cycle. At the shorter drying time of 12 hours, the FGMs formed from solutions containing the decomposing salt showed significantly lower residual moisture contents. Rapid dissolution of all the FGMs formed was observed on reconstitution.

4c. Effect of Viscosity Modifying Additive on FGM Formation

500 µl aliquots of 50–90% (w/v) trehalose solutions in deionized distilled water or PBS, containing 0.5–2% (w/v) guar gum (Jaguar HP60), were dried in 5 or 10 ml vials in the FTS drier for 16 hours. Initial shelf temperature and vacuum pressure of 30° C. and 30 Torr/mm Hg, respectively, were raised to 60° C. and 0.03 Torr/mm Hg after 2 hours and maintained at these values for the next 14 hours of the drying cycle. Representative examples of the FGMs formed are shown in FIG. 4. All FGMs again showed rapid dissolution on reconstitution in either water or PBS.

EXAMPLE 5

Illustrative Examples of FGM Formation

5a. Formation of FGM From Glass Matrix-forming Materials, Plus Additive, Incorporating Molecular Active Substance in Homogeneous Solution Formulations containing an active, alkaline phosphatase (1 mg/ml) in solution with a mixture of glass matrix-forming materials, trehalose [in a range of concentrations from 20–50% (w/v)] and HSA (2% w/v) plus volatile salt additive, ammonium bicarbonate (50 mM) were prepared in PBS or HEPES buffer. 250 µl volumes were aliquoted into 3 ml pharmaceutical vials and dried in the FTS drier. The shelf temperature was initially set at 30° C. and the vacuum pressure altered at 2 minute intervals from 30 Torr/mm Hg down to 25, 20, 15, 10 and finally 0.03 Torr/mm Hg before increasing the shelf temperature to 40° C. and finally 60° C. Total cycle time was approximately 20 hours. Residual moisture contents of resultant FGM's were approximately 1% w/w.

5b. Formation of FGM of Glass Matrix-forming Material Incorporating Mixtures of Molecular Active Substances in Homogeneous Suspension The commercial vaccine formulation of Hepatitis B surface antigen adsorbed onto the inorganic adjuvant aluminium hydroxide was dried in 300 µl volumes of 20% (w/v) trehalose in PBS, in 3 ml pharmaceutical vials. The FTS drying protocol involved a pressure of 0.03 Torr/mm Hg with shelf temperature maintained at 40° C. throughout a drying cycle of approximately 18 hours. Mean residual moisture contents of FGMs were approximately 4–4.5% w/w.

5c. Formation of FGM of Glass Matrix-forming Materials Incorporating Macromolecular Active Substances Formulations Dried to Obtain FGMs Contained Measles or Oral Polio Virus at the Required Dosages and comprised of:

i) 50% (w/v) trehalose+2% (w/v) HSA±50 mM ammonium bicarbonate
  ii) 50% (w/v) lactitol+2% (w/v) HSA±50 mM ammonium bicarbonate
  iii) 40% (w/v) trehalose+10% (w/v) sorbitol+2% (w/v) HSA±50 mM ammonium bicarbonate Samples were prepared using either PBS or HEPES buffer and 250 µl aliquots were dispensed into 3 ml pharmaceutical vials and dried in the FTS drier using two protocols.

a) For samples containing the volatile salt additive, ammonium bicarbonate vacuum pressure was altered at 2 minute intervals from 30, 25, 20, 15, 10 and finally 0.03 Torr/mm Hg. The shelf temperature was set at 30° C. initially before increasing to 40° C. Total cycle time was approximately 20 hours. Residual moisture contents were approximately 2% (w/v) and all showed rapid dissolution on reconstitution.
  b) For samples that contained no volatile salt additive, vacuum pressure was set immediately for 0.03 Torr/mm Hg and maintained throughout the 20 hour drying cycle. The shelf temperature was set at 30° C. initially before increasing to 40° C. The residual moisture contents of the FGMs formed were approximately 4% (w/w) and all showed rapid dissolution on reconstitution.

5d. Formation of FGM of Glass Matrix-forming Materials Incorporating Cellular Substances Drying Human Red Blood Cells 5% (v/v) hematocrit concentration of erythrocytes were formulated in either:

i) 50% (w/v) trehalose±50 mM ammonium bicarbonate
  ii) 25% (w/v) trehalose+10% (w/v) hydroxyethyl starch (HES) in PBS 200 μl aliquots were dried in 3 ml pharmaceutical vials in the FTS drier. The drying protocol used a constant shelf temperature of 37° C. and vacuum pressure was immediately reduced to 0.03 Torr/mm Hg. Cycle time was 18 hours. The resulting FGM's had residual moisture contents of 2.5–3% (w/w) and rehydrated rapidly on reconstitution.

Drying Human Blood Platelets

Platelets at an initial concentration of $500 \times 10^9$/L were dried in a formulation of 5% (w/v) trehalose in HEPES buffered saline containing 5 mM potassium chloride, 1 mM magnesium sulphate, 0.05 U/ml hirudin, 0.0125 U/ml apyrase, 10 μM indomethacin and 250 mM ammonium bicarbonate. 200 μl aliquots were dried in 3 ml pharmaceutical vials in the FTS drier. The drying protocol used a constant shelf temperature of 37° C. and vacuum pressure was reduced immediately to 0.03 Torr/mm Hg. Cycle time was 18 hours. The resulting FGM's had mean residual moisture contents of 1% (w/w) and rehydrated rapidly on reconstitution.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

What is claimed is:

1. A method for producing foamed glass matrices (FGMs) containing a biologically active agent, comprising the steps of:
   (a) preparing an initial mixture comprising at least one glass matrix-forming material containing a biologically active agent selected from the group consisting of a therapeutic agent, a prophylactic agent, a pharmaceutically effective substance and a diagnostic reagent, and an organic solvent(s) for the glass matrix-forming material;
   (b) evaporating a portion of the solvent(s) from the mixture to obtain a syrup;
   (c) boiling the syrup under less than atmospheric pressure to produce foaming of the syrup; and
   (d) continuing step (c) until the boiling results in the formation of a solid foam and produces a foamed glass matrix containing the biologically active agent.

2. A method for producing foamed glass matrices (FGMs) containing a biologically active agent, comprising the steps of:
   (a) preparing an initial mixture comprising at least one glass matrix-forming material containing a biologically active agent selected from the group consisting of a therapeutic agent, a prophylactic agent, a pharmaceutically effective substance and a diagnostic reagent, and a solvent(s) for the glass matrix-forming material, wherein the solvent(s) is a combination of aqueous and organic liquids;
   (b) evaporating a portion of the solvent(s) from the mixture to obtain a syrup;
   (c) boiling the syrup under less than atmospheric pressure to produce foaming of the syrup; and
   (d) continuing step (c) until the boiling results in the formation of a solid foam and produces a foamed glass matrix containing the biologically active agent.

3. A method for producing foamed glass matrices (FGMs) containing a biologically active agent, comprising the steps of:
   (a) preparing an initial mixture comprising at least one glass matrix-forming material containing a biologically active agent selected from the group consisting of a therapeutic agent, a prophylactic agent, a pharmaceutically effective substance and a diagnostic reagent, and solvent(s) for the class matrix-forming material;
   (b) evaporating a portion of the solvent(s) from the mixture to obtain a syrup;
   (c) boiling the syrup under less than atmospheric pressure to produce foaming of the syrup; and
   (d) continuing step (c) until the boiling results in the formation of a solid foam and produces a foamed glass matrix containing the biologically active agent;
   wherein the method further comprises the step of adding at least one volatile salt to the mixture before step (c).

4. The method according to claim 3, wherein the volatile salt is selected from the group consisting of ammonium acetate, ammonium bicarbonate, and ammonium carbonate.

5. The method according to claim 3, wherein the volatile salt is present in an amount from about 0.01 to 5 M.

6. A method for producing foamed glass matrices (FGMs) containing a biologically active agent, comprising the steps of:
   (a) preparing an initial mixture comprising at least one glass matrix-forming material containing a biologically active agent selected from the group consisting of a therapeutic agent, a prophylactic agent, a pharmaceutically effective substance and a diagnostic reagent, and solvent(s) for the glass matrix-forming material;
   (b) evaporating a portion of the solvent(s) from the mixture to obtain a syrup;
   (c) boiling the syrup under less than atmospheric pressure to produce foaming of the syrup; and
   (d) continuing step (c) until the boiling results in the formation of a solid foam and produces a foamed glass matrix containing the biologically active agent;
   wherein the method further comprises the step of adding at least one salt that decomposes under less than atmospheric pressure to give a gaseous product to the mixture before step (c).

7. The method according to claim 6, wherein the decomposing salt is selected from the group consisting of sodium bicarbonate and sodium metabisulphite.

8. A method for producing foamed glass matrices (FGMs) containing a biologically active agent, comprising the steps of:
   (a) preparing an initial mixture comprising at least one glass matrix-forming material containing a biologically active agent selected from the group consisting of a therapeutic agent, a prophylactic agent, a pharmaceutically effective substance and a diagnostic reagent, and solvent(s) for the glass matrix-forming material;
   (b) evaporating a portion of the solvent(s) from the mixture to obtain a syrup;
   (c) boiling the syrup under less than atmospheric pressure to produce foaming of the syrup; and
   (d) continuing step (c) until the boiling results in the formation of a solid foam and produces a foamed glass matrix containing the biologically active agent;
   wherein the method further comprises the step of adding at least one volatile organic liquid to the mixture before step (c).

9. A method for producing foamed glass matrices (FGMs) containing a biologically active agent, comprising the steps of:
   (a) preparing an initial mixture comprising at least one glass matrix-forming material containing a biologically active agent selected from the group consisting of a therapeutic agent, a prophylactic agent, a pharmaceutically effective substance and a diagnostic reagent, and solvent(s) for the glass matrix-forming material;

(b) evaporating a portion of the solvent(s) from the mixture to obtain a syrup;

(c) boiling the syrup under less than atmospheric pressure to produce foaming of the syrup; and (d) continuing step (c) until the boiling results in the formation of a solid foam and produces a foamed glass matrix containing the biologically active agent;

wherein the method further comprises the step of adding at least one additive to the mixture before step (c), wherein the additive is a foam stabilizing agent, wherein the foam stablization agent is a viscosity modifier, and wherein the viscosity modifier is a guar gum.

10. A method for producing foamed glass matrices (FGMs) containing a biologically active agent, comprising the steps of:

(a) preparing an initial mixture comprising at least one glass matrix-forming material containing a biologically active agent selected from the group consisting of a therapeutic agent, a prophylactic agent, a pharmaceutically effective substance and a diagnostic reagent, and solvent(s) for the glass matrix-forming material;

(b) evaporating a portion of the solvent(s) from the mixture to obtain a syrup;

(c) boiling the syrup under less than atmospheric pressure to produce foaming of the syrup; and (d) continuing step (c) until the boiling results in the formation of a solid foam and produces a foamed glass matrix containing the biologically active agent;

wherein the method further comprises the step of adding at least one additive to the mixture before step (c), wherein the additive is a foam stabilizing agent, and wherein the foam stabilization agent is a surface-active amphipathic molecule.

11. A method for producing foamed glass matrices (FGMs) containing a biologically active agent, comprising the steps of:

(a) preparing an initial mixture comprising at least one glass matrix-forming material containing a biologically active agent selected from the group consisting of a therapeutic agent, a prophylactic agent, a pharmaceutically effective substance and a diagnostic reagent, and solvent(s) for the glass matrix-forming material;

(b) evaporating a portion of the solvent(s) from the mixture to obtain a syrup;

(c) boiling the syrup under less than atmospheric pressure to produce foaming of the syrup; and (d) continuing step (c) until the boiling results in the formation of a solid foam and produces a foamed glass matrix containing the biologically active agent;

wherein the method further comprises the step of adding at least additive that is an inhibitor of the Maillard reaction to the mixture before step (c).

12. A method for preserving a biologically active agent within a foamed glass matrix (FGM) comprising the steps of:

(a) preparing an initial mixture comprising at least one glass matrix-forming material containing a biologically active agent to be preserved and solvent(s) for the class matrix-forming material;

(b) evaporating a portion of the solvent(s) from the mixture to obtain a syrup;

(c) boiling the syrup under less than atmospheric pressure to produce foaming of the syrup; and (d) continuing step (c) until the boiling results in the formation of a solid foam and produces a foamed glass matrix containing the biologically active agent;

wherein the biologically active agent to be preserved is a vaccine; and wherein the vaccine comprises Hepatitis B Surface Antigen, measles virus, or oral polio virus.

13. A method for preserving a biologically active agent within a foamed glass matrix (FGM) comprising the steps of:

(a) preparing an initial mixture comprising at least one glass matrix-forming material containing a biologically active agent to be preserved selected from the group consisting of a therapeutic agent, a prophylactic agent, a pharmaceutically effective substance and a diagnostic reagent and solvent(s) for the glass matrix-forming material;

(b) evaporating a portion of the solvent(s) from the mixture to obtain a syrup;

(c) boiling the syrup under less than atmospheric pressure to produce foaming of the syrup; and (d) continuing step (c) until the boiling results in the formation of a solid foam and produces a foamed glass matrix containing the biologically active agent;

wherein the biologically active agent to be preserved is dissolved in the mixture.

* * * * *